(12) United States Patent
Raphael et al.

(10) Patent No.: US 7,008,455 B2
(45) Date of Patent: Mar. 7, 2006

(54) LIP IMPLANT, INSTRUMENTATION AND METHOD FOR INSERTION

(75) Inventors: Peter Raphael, Plano, TX (US); Scott Harris, Dallas, TX (US)

(73) Assignee: Surgisil, L.L.P., Plano, TX (US)

( * ) Notice: Subject to any disclaimer, the term of this patent is extended or adjusted under 35 U.S.C. 154(b) by 110 days.

(21) Appl. No.: 10/384,229

(22) Filed: Mar. 7, 2003

(65) Prior Publication Data

US 2004/0176856 A1  Sep. 9, 2004

(51) Int. Cl.
*A61F 2/04* (2006.01)
(52) U.S. Cl. .................. 623/23.64; 623/15.11; 623/23.72; 623/11.11
(58) Field of Classification Search ............ 623/11.11, 623/23.64, 23.72, 66.1, 15.11
See application file for complete search history.

(56) References Cited

U.S. PATENT DOCUMENTS

| | | | |
|---|---|---|---|
| 5,030,232 A | 7/1991 | Pham | |
| 5,195,951 A * | 3/1993 | Giampapa | 623/17.17 |
| 5,258,028 A | 11/1993 | Ersek et al. | |
| 5,413,600 A | 5/1995 | Mittelman | |
| 5,496,371 A | 3/1996 | Eppley et al. | |
| 5,571,182 A | 11/1996 | Ersek et al. | |
| 5,578,050 A * | 11/1996 | Webb | 606/167 |
| 5,607,477 A | 3/1997 | Schindler et al. | |
| 5,782,913 A | 7/1998 | Schindler et al. | |
| 5,941,909 A | 8/1999 | Purkait | |
| 5,941,910 A | 8/1999 | Schindler et al. | |
| 6,083,262 A | 7/2000 | Caravel | |
| 6,083,912 A | 7/2000 | Khouri | |
| 6,129,761 A | 10/2000 | Hubbell | |

* cited by examiner

*Primary Examiner*—Corrine McDermott
*Assistant Examiner*—William H Matthews
(74) *Attorney, Agent, or Firm*—Haynes and Boone, LLP

(57) ABSTRACT

A lip implant and lip instrument. The lip implant is formed of solid silicone and is shaped to be received in the lip of a patient. The lip instrument includes a pair of arms coupled together having clamping members to grasp and retain the lip implant. A method for insertion of the lip implant into the patient is further described.

8 Claims, 2 Drawing Sheets

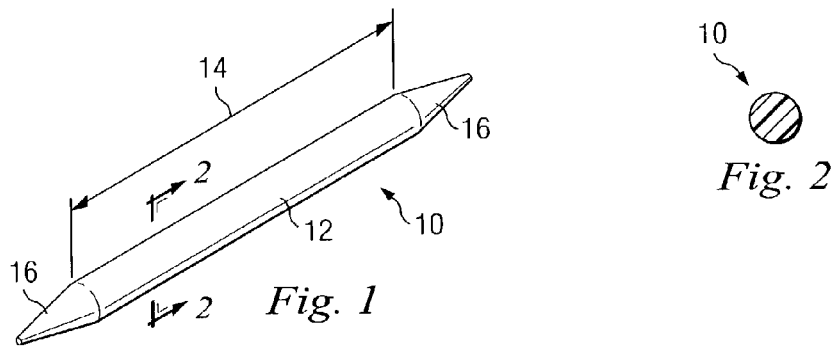
Fig. 1
Fig. 2
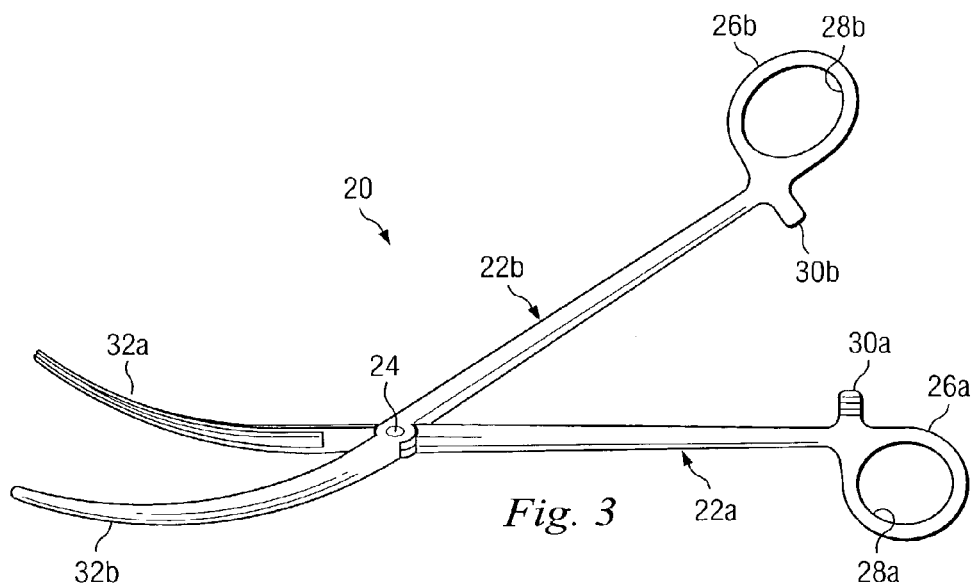
Fig. 3
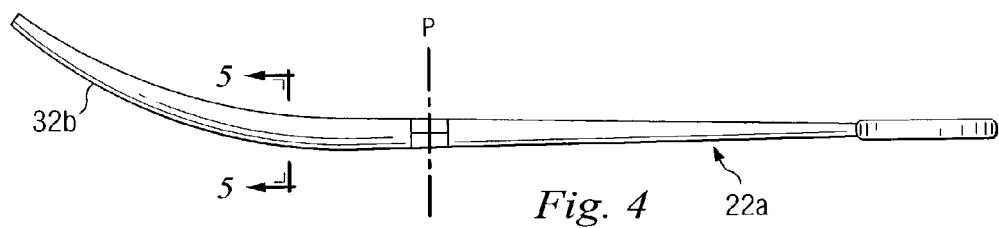
Fig. 4

LIP IMPLANT, INSTRUMENTATION AND METHOD FOR INSERTION

BACKGROUND

The present disclosure relates generally to a lip implant, and more particularly to a silicone lip implant for purposes of lip augmentation and a method for insertion of the lip implant.

Plastic surgery, such as soft tissue augmentation, has long been a popular surgical technique for people wanting to enhance their physical appearance. More recently, lip augmentation, to increase the fullness of the lips, has increasingly become a viable plastic surgery option.

Currently, there are a variety of materials and methods used for lip augmentation. Some of the current techniques provide for temporary lip augmentation via injection of various materials into the lip such as fat, collagen, hyaluronic acid, and particulated dermis or fascia. One of the disadvantages of such temporary techniques is the need for the patient to periodically undergo additional procedures to maintain the lip fullness resulting from the temporary lip augmentation.

Other techniques, such as liquid silicone injections, provide for more permanent lip augmentation. However, liquid silicone injections carry the potential for various problems such as skin ulceration, long-term nodularity and granuloma formation, and chronic cellulitis. Furthermore, it is inherently difficult to remove liquid silicone from the lips should a problem arise or should the patient desire removal.

Other permanent lip augmentation techniques include the implantation of various forms of expanded polytetraflouroethylene (PTFE) such as Gore-Tex® strips or tubular forms of PTFE such as Softform® and Ultrasoft™. Expanded PTFE utilizes the concept of tissue ingrowth into the porous wall of the implant. While beneficial in some areas of the body, implantation of such material into the lips can be detrimental due to the tissue adherence to the implant, which often results in a restriction of lip excursion with an abnormal appearance of facial expression. Furthermore, fluid may accumulate in the tubular forms of PTFE, thereby resulting in an unacceptably high incidence of surgical infection with subsequent loss of implant.

Therefore, what is needed is a lip implant that eliminates, or at least reduces, the above-described problems. Furthermore, instrumentation, and a method for insertion of the lip implant is needed.

BRIEF DESCRIPTION OF THE DRAWINGS

FIG. 1 is a perspective view of a lip implant according to one embodiment of the present disclosure.

FIG. 2 is a cross-sectional view of the lip implant of FIG. 1 taken along the line 2—2.

FIG. 3 is a perspective view of a lip implant instrument according to one embodiment of the present disclosure.

FIG. 4 is a side view of the lip implant instrument of FIG. 3.

DESCRIPTION

Figure 5:
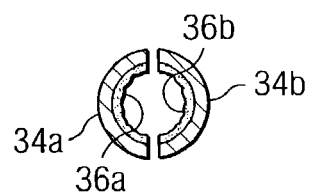
FIG. 5 is a cross-sectional view of the lip implant instrument of FIG. 4 taken along the line 5—5.

Referring to FIG. 1, a lip implant for implantation into a lip of a patient (not shown) is generally referred to by reference numeral 10. The lip implant is integrally formed of silicone, such as medical grade silicone, and is substantially solid as shown in the cross-section of FIG. 2.

The lip implant 10 is formed to have a substantially uniform level of hardness as can be measured by the durometer A-scale rating of the lip implant. In one embodiment, the lip implant 10 has a durometer rating of five (5) resulting in a relatively soft lip implant. In such an embodiment, the lip implant 10 includes a skin 12, also formed of silicone, having a higher durometer rating to provide the lip implant with structural integrity and manageability. Of course, the durometer rating of the lip implant 10 may vary depending on the particular hardness desired. For example, the lip implant 10 may be formed to have a durometer rating of ten (10), thereby eliminating the need for the skin 12.

The lip implant 10 is shaped to have a substantially circular cross-section (FIG. 2). The diameter of the lip implant 10 is substantially uniform along the longitudinal axis of a middle portion 14 of the lip implant. The diameter of the middle portion 14 of the lip implant 10 can vary depending on the desired thickness of the lip implant. For instance, the diameter of the lip implant 10 may be between 2–10 millimeters.

The middle portion 14 of the lip implant 10 defines a pair of end portions 16. The end portions 16 are tapered in diameter such that the diameter of the lip implant 10 along the end portions decreases from the middle portion 14 to the ends of the lip implant. The middle portion 14 and the end portions 16 of the lip implant 10 cooperate to define the length of the lip implant, which can vary depending on the desired length of the lip implant. For instance, the length of the lip implant 10 may be between 5–8 centimeters.

Referring to FIGS. 3–5, a lip instrument for use in implanting the lip implant 10 is generally referred to by reference numeral 20. The lip instrument 20 includes a pair of arms 22a, 22b coupled together at a pivot point 24 in any conventional manner to provide for relative pivotal movement of the arms about a pivotal axis P (FIG. 4). Proximal to the pivotal axis P, the arms 22a, 22b include a pair of integrally formed ring-like members 26a, 26b, respectively, which define a pair of finger openings 28a, 28b. A pair of protrusions 30a, 30b extend towards one another from the ring-like members 26a, 26b, respectively, to prevent over-rotation of the arms 22a, 22b.

Distal to the pivotal axis P, the arms 22a, 22b include a pair of integrally formed curved clamping members 32a, 32b, respectively, which cooperate to grasp the lip implant 10 (FIG. 1) as will be further described with respect to the method of insertion. Referring to FIG. 5, the clamping members 32a, 32b include an outer generally convex surface 34a, 34b, respectively, and a corresponding inner generally concave surface 36a, 36b.

The inner surfaces 36a, 36b of the clamping members 32a, 32b face one another such that closing of the clamping members defines a generally circular area for receiving the lip implant 10 (FIG. 1). The inner surfaces 36a, 36b are formed of carbide to protect against crushing of the lip implant 10 (FIG. 1) when grasped by the clamping members.

Figure 6:
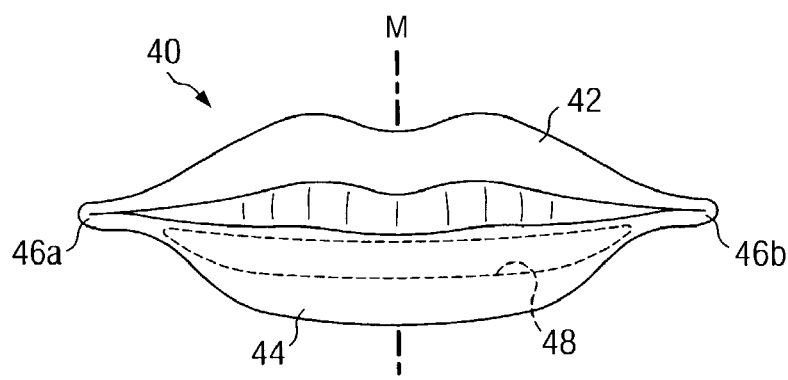
FIG. 6 is a schematic view of a lip for receiving the lip implant according to the present disclosure.

Referring to FIG. 6, a lip region 40 of a patient (not shown) to receive the lip implant is depicted. The lip region 40 includes an upper lip 42 and a lower lip 44, which meet at a pair of commissures 46a, 46b. The commissures 46a, 46b are substantially equidistant from a midline M of the lip region 40. A tunnel 48, as is generally illustrated in phantom in FIG. 6, is formed through the lower lip 44 for reasons to be described with respect to the method for insertion.

Method for Insertion

In operation and referring to FIG. 6, the lip region 40 is prepared for insertion of the implant by administering a local anesthetic, such as lidocaine with epinephrine, to the lips. Incisions are then made at each commissure 46a, 46b of the lip region 40 via a conventional scalpel. For sake of clarity, the method of insertion will be described with respect to insertion of the lip implant 10 into the lower lip 44 although it will be understood that the lip implant can be inserted into the upper lip 42 as well.

Initial formation of the tunnel 48 is then performed with conventional curved iris scissors (not shown). The iris scissors are inserted into the lower lip 44 via the incision at commissure 46a to dissect the tunnel 48 towards the midline M of the lip region 40. In a like manner, the iris scissors are then inserted through the incision at commissure 46b on the opposite side of the lip region 40 to dissect the tunnel 48 towards the midline M of the lip region. Such dissection culminates in the initial formation of the tunnel 48 through the lower lip 44. The tunnel 48 is then widened via manipulation of the iris scissors to complete the formation of the tunnel.

Upon formation of the tunnel 48, the lip instrument 20 is inserted into the lower lip 44 via the incision at commissure 46a and the tunnel 48 such that the clamping members 32a, 32b extend through the tunnel and a portion of the clamping members extends out of the incision at commissure 46b. The lip instrument 20 is then actuated to grasp the lip implant 10 in the clamping members 32a, 32b. The lip implant 10 is then drawn into the lower lip 44 via the lip instrument 20 until it is seated appropriately within the tunnel 48 whereupon the lip implant is released from the lip instrument.

A conventional suture, such as a chromic suture, is applied to close the incisions at commissures 46a, 46b. Antibiotic ointment is then applied to the incisions at commissures 46a, 46b to reduce the risk of infection. Ice is applied indirectly to the lip region 40 to further aid in the healing process.

Thus, as described, insertion of the lip implant 10 is accomplished simply and quickly and in an uninterrupted technique. Furthermore, the problems associated with previous lip augmentation techniques can be overcome with the use of the lip implant 10.

ALTERNATES AND EQUIVALENTS

It is understood that a variety of alternative lip implants are contemplated by this disclosure. For example, and referring now to FIG. 7, a lip implant 70 substantially similar in all respects to the lip implant 10 of FIGS. 1 and 2, other than those features described below, has a middle portion 72 that includes a section 74 having a non-uniform diameter.

In another alternative embodiment, and referring now to FIG. 8, a lip implant 80 substantially similar in all respects to the lip implant 10 of FIGS. 1 and 2, other than those features described below, includes a middle portion 82 having a non-uniform diameter along the entire length of the middle portion.

Figure 7:
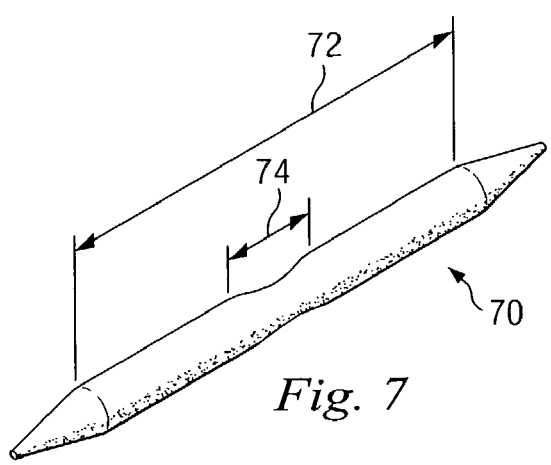
FIG. 7 is a perspective view of a lip implant according to another embodiment of the present disclosure.
Figure 8:
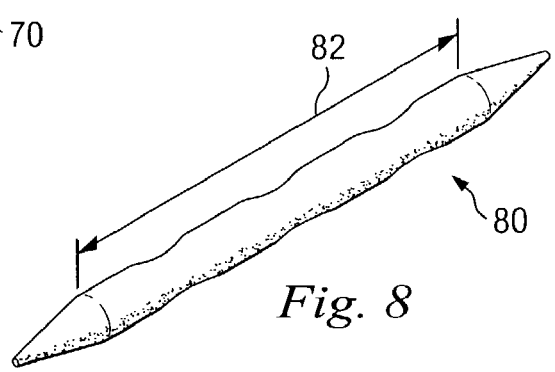
FIG. 8 is a perspective view of a lip implant according to yet another embodiment of the present disclosure.

In operation, the lip implants 70 and 80 of FIGS. 7 and 8, respectively, are inserted into the lower lip 44 (FIG. 6) of the patient in a substantially similar manner as described above. Thus, the embodiments of FIGS. 7 and 8 enjoy the advantages of that of FIG. 1 with respect to providing a structurally sound and safe lip implant for lip augmentation purposes.

While the invention has been particularly shown and described with reference to embodiments thereof, it is understood by those skilled in the art that various changes in form and detail may be made therein without departing from the spirit and scope of the invention. For example, although a plurality of shapes for the lip implant 10 are described, these shapes are merely representative of the variety of shapes that the lip implant may take. Thus, the lip implant 10 is not limited to the longitudinal or cross-sectional shapes as described.

Moreover, the tapered end portions 16 of the lip implant 10 may be removed resulting in a lip implant having a rod-like shape. Still further, the degree of taper and the length of the end portions 16 may be varied to accommodate the various desires of implant patients.

Furthermore, the lip implant 10 may be partially hollow to accommodate a liquid such as liquid silicone or saline. In such an embodiment, the lip implant 10 includes a solid outer portion of silicone that encloses a liquid inner portion.

Still further, the clamping members 32a, 32b of the lip instrument 20 may be removably attached to the lip instrument such that various other clamping members may be used therewith. For instance, various degrees of curvature may be required of the clamping members resulting in the need to interchange the clamping members.

Furthermore, the inner surfaces 36a, 36b of the clamping members 32a, 32b may be formed of a variety of materials other than carbide.

Still further, during insertion of the lip implant 10 into the lower lip 44, the incision may be made in the general commissure region on each side of the lip region 40 and such insertion is not limited to an exact commissure point.

It is also understood that all spatial references, such as "diameter", "longitudinal," "increase," and "decrease" are for illustrative purposes only and can be varied within the scope of the invention. Accordingly, all such modifications are intended to be included within the scope of this invention as defined in the following claims.

What is claimed is:

1. A lip implant, comprising:
   solid silicone shaped to correspond to the shape of a lip, the solid silicone comprising
      a middle portion having a geometric center point and a substantially uniform diameter between 2 millimeters and 10 millimeters;
      a pair of substantially symmetric end portions, each end portion having a tapered diameter; and
      a length between 5 centimeters and 8 centimeters;
   wherein the solid silicone is substantially symmetric in all directions about the geometric center point of the middle portion.

2. The lip implant of claim 1 wherein the solid silicone is medical grade silicone.

3. The lip implant of claim 1 wherein the lip implant is formed to have a substantially uniform level of hardness.

4. The lip implant of claim 1 wherein the lip implant is shaped to have a substantially circular cross-section.

5. The lip implant of claim 1 wherein the middle portion and the end portions cooperate to define the length of the lip implant.

6. The lip implant of claim 1 wherein the solid silicone has a durometer A-scale rating of 5.

7. The lip implant of claim 1 wherein the solid silicone has a durometer A-scale rating of 1.

8. The lip implant of claim 1 wherein the solid silicone has a durometer A-scale rating of between 5 and 1.

* * * * *

UNITED STATES PATENT AND TRADEMARK OFFICE
CERTIFICATE OF CORRECTION

PATENT NO. : 7,008,455 B2
DATED : March 7, 2006
INVENTOR(S) : Raphael et al.

It is certified that error appears in the above-identified patent and that said Letters Patent is hereby corrected as shown below:

Column 4,
Lines 63 and 65, change "1" to -- 10 --.

Signed and Sealed this

Sixth Day of June, 2006

JON W. DUDAS
*Director of the United States Patent and Trademark Office*